United States Patent [19]
Pilgrimm

[11] Patent Number: 5,916,539
[45] Date of Patent: Jun. 29, 1999

[54] SUPERPARAMAGNETIC PARTICLES, PROCESS FOR PRODUCING THE SAME AND THEIR USE

[75] Inventor: Herbert Pilgrimm, Berlin, Germany

[73] Assignee: Silica Gel Ges. m.b.H., Berlin, Germany; a part interest

[21] Appl. No.: 08/530,132

[22] PCT Filed: Mar. 17, 1994

[86] PCT No.: PCT/DE94/00314

§ 371 Date: Sep. 12, 1995

§ 102(e) Date: Sep. 12, 1995

[87] PCT Pub. No.: WO94/21240

PCT Pub. Date: Sep. 29, 1994

[30] Foreign Application Priority Data

Mar. 2, 1993 [DE] Germany ............................. 44 07 338
Mar. 17, 1993 [DE] Germany ............................. 43 09 333

[51] Int. Cl.⁶ .................................................. A61B 5/055
[52] U.S. Cl. ...................... 424/9.322; 424/646; 424/648; 514/54
[58] Field of Search ................................ 424/9.322, 646, 424/648; 514/54, 57, 59; 128/653.4, 654; 436/173; 423/632, 633

[56] References Cited

U.S. PATENT DOCUMENTS

| | | | |
|---|---|---|---|
| 3,917,538 | 11/1975 | Bass ........................................ | 514/294 |
| 3,933,997 | 1/1976 | Hersh ...................................... | 436/526 |
| 3,970,518 | 7/1976 | Giaever ................................... | 435/239 |
| 4,101,435 | 7/1978 | Hasegawa ............................. | 252/62.53 |
| 4,152,210 | 5/1979 | Robinson ............................. | 435/173.2 |
| 4,177,253 | 12/1979 | Davies .................................... | 436/526 |
| 4,230,685 | 10/1980 | Senyei .................................... | 436/526 |
| 4,267,234 | 5/1981 | Rembaum ............................. | 428/403 |
| 4,343,901 | 8/1982 | De Filippi ............................. | 435/176 |
| 4,452,773 | 6/1984 | Molday ................................. | 424/1.37 |
| 4,554,088 | 11/1985 | Whitehead ........................... | 252/65.54 |
| 4,615,879 | 10/1986 | Runge .................................... | 424/9.32 |
| 4,675,173 | 6/1987 | Widder ................................ | 424/9.322 |
| 4,767,611 | 8/1988 | Gordon ........................................ | 424/9 |
| 4,863,715 | 9/1989 | Jacobsen et al. .......................... | 424/9 |
| 4,925,678 | 5/1990 | Ranney ................................... | 424/493 |
| 5,069,216 | 12/1991 | Groman et al. ..................... | 424/9.322 |
| 5,160,725 | 11/1992 | Pilgrimm ............................ | 424/9.322 |
| 5,225,282 | 7/1993 | Chagnon et al. ....................... | 428/407 |
| 5,314,679 | 5/1994 | Lewis et al. ......................... | 424/9.322 |
| 5,328,681 | 7/1994 | Kito et al. ............................ | 424/9.322 |
| 5,349,957 | 9/1994 | Yudelson ............................. | 128/653.4 |
| 5,358,702 | 10/1994 | Unger ................................... | 424/9.322 |

FOREIGN PATENT DOCUMENTS

| | | |
|---|---|---|
| 125995 | 5/1984 | European Pat. Off. . |
| 284549 | 3/1988 | European Pat. Off. . |
| 516252 | 4/1992 | European Pat. Off. . |
| WO88/00060 | 1/1988 | WIPO . |
| WO90/01899 | 3/1990 | WIPO . |
| WO90/01295 | 8/1990 | WIPO . |

OTHER PUBLICATIONS

Meyers, P.H. et al., J.Am. J. Roentgenol, Radium Ther. Nucl. Med., 90,1068, 1963.
Frei, F.H. et al., J Appl. Phys., 39,999, 1968.
Nakamura et al., J. Appl. Phys., 42,1320, 1971.
Nature 270,259, 1977.
J. Allergy Clin. Immunol. 61,23, 1978.
Clin. Chem. 26,730, 1980.
Clin. Chem., 26,281, 1980.
Ito, R., et al., Int. J. Pharm., 61,109 1990.
Roch et al, Magma vol. 1, No. 2, 1993, pp. 83–88.

*Primary Examiner*—Gary E. Hollinden
*Attorney, Agent, or Firm*—Collard & Roe, P.C.

[57] ABSTRACT

New superparamagnetic particles useful in medicine for destroying tumors, increasing immunity and diagnosing conditions are disclosed. For that purpose, very small superparamagnetic single-domain particles are aggregated and protected against further aggregation by chemical bonding of reactive stabilizer substances on the surface of the superparamagnetic particles. These new particles thus consist of stable, decomposable aggregates with a particle size in a range between 10 and 1000 nanometers and a defined behavior in a magnetic field. The aggregates consist of several small superparamagnetic single-domain particles of iron oxide, iron mixed oxide or iron, with a particle size in a range between 3 and 20 nanometers, bearing on their surface chemically bound organic substances from the group comprising the phosphate, diphosphate, polyphosphate, thiophosphate, phosphonate or group containing polyalkylene glycols, phosphate group containing nucleotides, their oligomers or polymers, as well as phosphate group containing carbohydrates, which may present further binding sites. Both the new disclosed superparamagnetic aggregates and reactive stabilizer substances may be active substances.

12 Claims, No Drawings

SUPERPARAMAGNETIC PARTICLES, PROCESS FOR PRODUCING THE SAME AND THEIR USE

The invention relates to superparamagnetic particles which have chemically bound substances on their surface, optionally possess further binding sites for coupling tissue-specific binding substances, diagnostic or pharmacologically acting substances and to new related compounds and to the use of these particles and compounds in medicine for destroying tumours, increasing immunity and diagnosing conditions.

Magnetic particles have been described in a plurality of publications and patents, in particular for magnetic separation techniques and for use as contrast agents in NMR diagnosis.

In the sixties, attempts were made to use ferromagnetic particles as contrast agents for X-ray diagnosis and for magnetically controlled drug targeting, for example, Meyers, P. H. et al. J. Am. J. Roentgenol. Radium Ther. Nucl. Med., 90,1068.1963; Frei, F. H. et al. J. Appl. Phys., 39,999,1968; Nakamura et al. J. Appl. Phys., 42,1320,1971. The irreversible aggregation of the magnetic particles under the influence of a magnetic field proved to be a problem during in vivo application. The same applies to DE-A-3590398, U.S. Pat. No. 4,675,173, U.S. Pat. No. 4,615,879, WO 84/02643, GB-A-8408127 and WO 84/04330. Ferromagnetic particles with Weiss' domains of the order of a few hundred to a few thousand Angstrom units provided with a polymer coating to enable substances having a binding affinity for tissue to be coupled are proposed here.

Ferromagnetic particles of the suggested size have such great magnetic moments that the particles agglomerate to form greater aggregates even when they are provided with a polymer coating. The particles exist in aggregate form even during the coating process. Such ferromagnetic particles would sediment in the body during parenteral administration and the toxic side effects would be great.

Similar drawbacks also apply to the dispersions of ferromagnetic particles used in DE-A-3443251 and DE-A-3443252, where the magnetic interactions between the particles lead to aggregation and sedimentation. The irreversible sedimentation of the magnetic particles takes place very rapidly, particularly under the influence of magnetic fields. If there are inhomogeneities in the magnetic field, the magnetic particles invariably concentrate at the points with high field strengths. These drawbacks occur in particular during NMR diagnosis and during magnetic drug targeting, and very great irreversible aggregates of particles can be formed, giving rise to a great risk of embolism.

Even greater ferromagnetic particles are described in U.S. Pat. No. 3,933,997, U.S. Pat. No. 3,652,761, Nature 270,259,1977, J. Allergy Clin. Immunol. 61,23,1978, U.S. Pat. No. 4,177,253, Clin. Chem., 26,730,1980, Clin. Chem., 26,1281,1980, U.S. Pat. No. 3,970,518, U.S. Pat. No. 4,230, 685, U.S. Pat. No. 4,267,234, U.S. Pat. No. 4,152,210, U.S. Pat. No. 4,343,901. These magnetic particles with diameters between 10 and 160 $\mu$m can be separated even with weak magnetic fields but have the drawback that they sediment very rapidly, possess a small specific surface area for the binding of pharmacologically active substances, agglomerate irreversibly in the magnetic field and are too large for drug targeting owing to the risk of embolism.

The irreversible agglomeration of the magnetic particles in the magnetic field can be avoided by using superparamagnetic particles. Superparamagnetic particles have no remanence, i.e. they can be moved and concentrated reversibly in a magnetic gradient field. These superparamagnetic particles include, for example, iron oxides having a particle diameter smaller than 0.02 $\mu$m.

To prevent these superparamagnetic particles from sedimenting in aqueous dispersions, stabilizer substances which attach themselves to the particle surfaces by adsorption are added.

Such particles are described in U.S. Pat. No. 3,215,572, U.S. Pat. No. 3,531,413, U.S. Pat. No. 3,917,538, WO 85/02772, U.S. Pat. No. 4,101,435 and U.S. Pat. No. 4,452, 773, SE-A-8307060-7.

The adsorption-stabilized magnetic particles are not stable under physiological conditions as the magnetic particles easily aggregate owing to the release of the stabilizer substances. If substances with a binding affinity for specific tissue or pharmacological activity are coupled to adsorption-stabilized magnetic particles, there is a risk that the stabilizer substances and therefore the substances with binding affinity and pharmacological activity will be released from the magnetic particles and that the magnetic particles will not reach the binding site or the pharmacologically active substance will not be enriched at the site of action during magnetic drug targeting.

Aggregates of biodegradable superparamagnetic metal oxide crystals are known from WO 90/01889, in which the individual superparamagnetic crystals form aggregates with the polyfunctional substances owing to the addition of polyfunctional substances. The production of these aggregates corresponds to the procedure in WO 88/00060, according to which the iron oxide particles are precipitated from a solution additionally containing a polyfunctional substance such as polysaccharide, protein, etc., in the basic medium to form, for example, polysaccharide-coated superparamagnetic iron oxide particles which are then dialyzed and finally centrifuged. The precipitated particles are thus aggregated.

WO 90/01295 relates to MR contrast agents consisting of superparamagnetic metal oxides in association with macromolecular compounds or conjugates of these molecules with other polymeric substances which are produced in a similar manner to those in WO 88/00060.

A process for obtaining in vivo MR images of the gastro-intestinal tract is described in U.S. Pat. No. 5,069, 216, in which the superparamagnetic aggregates from WO 90/01295 or WO 88/00060 are used. EP-A-125 995 relates to magnetic particles with a magnetic metal oxide core having a silane coating on which molecules can be covalently coupled.

Roch, A. et al have described, in Magma 1 (1993) 83–88, superparamagnetic contrast agents consisting of agglomerates which are produced in the normal manner by addition of, for example, dextran to iron salt solutions.

EP-A-516 252 describes nanocrystalline magnetic particles with a coating of chemisorbed glycosaminoglycanes which run from iron salts via biomimetic synthesis in the neutral range at ambient temperature and without ultrasonic treatment.

In EP-A-0284549, the stabilizer substances contain phosphate or phosphonate groups by means of which they are chemically bound to the surface of the superparamagnetic particles. If the stabilizer substances still contain chemically reactive groups, pharmacologically active substances can be coupled. These chemically stabilized superparamagnetic particles do not sediment in aqueous dispersions and only have a diameter of 0.003 to 0.01 $\mu$m. There is no release of the stabilizer substances during parenteral administration, i.e. there is no aggregation and sedimentation in the blood and therefore good distribution in the organism.

These magnetic particles are too small for magnetic drug targeting as very great magnetic field gradients would have to be used in order to enrich the magnetic particles in specific regions of the body.

Greater superparamagnetic particles can be produced by encapsulating small 0.01 $\mu$m-sized superparamagnetic particles in porous polymer particles (SE-A-7706431), polyglutaraldehyde polymers (U.S. Pat. No. 4,267,234), silane polymers (U.S. Pat. No. 4,554,088), albumin condensation polymers (U.S. Pat. No. 4,675,173) or cellulose esters (Ito, R. et al., Int. J. Pharm., 61,109,1990). The particle diameters are in the range of 0.05 to 100 $\mu$m. Apart from the albumin condensation polymers and the cellulose esters, all polymerization chemicals used are physiologically harmful and the dissolution rate of the magnetic particles in the body very slow. All above-mentioned larger superparamagnetic particles sediment in the gravitational field of the earth and therefore have to be dispersed again prior to use.

The iron oxide contents of the polymer particles lie in the range of 10 to a maximum of 50% by weight and the volumetric content at a maximum of 10% by volume. The smaller the magnetic particles, the higher the magnetic field gradients required during magnetic drug targeting in order to concentrate the magnetic particles in specific regions of the body. The greater the magnetic particles, the faster they are bound by the reticuloendothelial system, i.e. the biocompatibility is reduced and the content of bound pharmacologically active substance diminishes. Therefore, optimum magnetic particles for magnetic drug targeting should be as small as possible and have the greatest possible loading with pharmacologically active substances, the highest possible content of magnetic material, the greatest possible magnetic permeability of the magnetic material, the greatest possible dissolution rate in the body and adequate biocompatibility in the body.

The object of the invention specified in claim 1 is to produce new compounds and superparamagnetic particles in order to avoid the drawbacks mentioned at the outset and to open up new spheres of application, in particular in destroying tumours and increasing immunity.

According to the invention, this is achieved in that very small superparamagnetic single-domain particles are aggregated and protected from further aggregation by the chemical binding of reactive stabilizer substances on the surface of the superparamagnetic particles. The new superparamagnetic aggregates as well as the reactive stabilizer substances can be active substances in the sense of the invention.

In contrast to the prior art, aggregation of the single-domain particles takes place first and then the binding of the stabilizer substances to the aggregate surface, yielding other properties of the aggregates.

The superparamagnetic particles according to the invention, consisting of single-domain particles and stabilizer substances, are therefore characterized in that superparamagnetic single-domain particles consisting of iron oxide, iron mixed oxide or iron with a particle size in the range between 3 and 20 nanometers are combined to form stable, decomposable aggregates exhibiting defined behaviour in the magnetic field, with a particle size of the aggregates in the range between 10 and 1000 nanometers, wherein the aggregates have a monomolecular layer on their surface, consisting of stabilizer substances from the group comprising the phosphate, diphosphate, carboxylate, polyphosphate, thiophosphate, phosphonate, thiophosphonate, sulphate, sulphonate, mercapto, silanetriol, trialkoxysilane group-containing polyalkylene glycols, the carbohydrates or the phosphate group-containing nucleotides, their oligomers or their polymers, which can have further binding sites.

It is advantageous to produce the superparamagnetic single-domain particles as small as possible in order to keep the biological decomposition high and the toxicity as low as possible. The superparamagnetic single-domain particles are in the diameter range of 0.001 to 0.02 $\mu$m, preferably in the range of 0.003 to 0.01 $\mu$m.

$\gamma$-$Fe_2O_3$, $Fe_3O_4$ and Fe are used as physiologically compatible materials for in vivo application. More toxic magnetic materials can also be used for in vitro applications, such as iron mixed oxides corresponding to the general formula $MO.Fe_2O_3$3, wherein M represents the divalent metal ions Fe, Mg, Be, Mn, Zn, Co, Ba, Sr, Cu or mixtures thereof or such as iron mixed oxides corresponding to the general formula $mFe_2O_3.nMe_2O_3$, wherein Me represents the trivalent metal ions Al, Cr, rare earth metals or mixtures thereof.

According to the invention, the superparamagnetic single-domain particles are aggregated by thermal treatment in an aqueous dispersion by altering the pH, the temperature and optionally the pressure. It has surprisingly been found that the superparamagnetic single-domain particles agglomerate to larger superparamagnetic particles when the pH of the precipitation dispersion changes from between 8.0 and 10.0 to between pH 3.0 and 7.0 and with heating to temperatures of between 50 and 120° C. Surprisingly, crystal growth does not occur, which would lead to ferromagnetic particles, but rather mere aggregation of the single-domain particles to larger assemblies of particles, so the superparamagnetic character of the aggregates is maintained. The stability of the aggregates is sufficiently great for only a small proportion of stabilized superparamagnetic single-domain particles to be formed by the subsequent addition of the stabilizer substances. Different particle diameters in close diameter ranges can be produced according to pH, temperature, temperature gradient, aggregation time, type of electrolyte and electrolyte concentration of the aqueous dispersion. The lower the pH of the dispersion, the greater the aggregates. A rise in temperature and an extension of the aggregation time act in the same direction. Increasingly greater ferromagnetic particles which are unsuitable for the application according to the invention are formed if the aggregation times are too long. The type of electrolyte and the concentration of electrolyte also act, via the thickness of the electrochemical double layer of the superparamagnetic single-domain particles, on particle aggregation.

The particle diameters which can be produced lie in the range of 0.01 to 10 $\mu$m, but preferably in the range of 0.02 to 1 $\mu$m, in particular in the range of 0.02 to 0.5 $\mu$m. The small particles are preferred on account of their large surface area and the associated greater binding of active ingredient.

According to the invention, the magnetic particles are stabilized by the chemical binding of phosphate-containing radicals, selected from monophosphate, diphosphate, polyphosphate, phosphonate, thiophosphate, thiophosphonate or a carboxylate, sulphate, sulphonate, mercapto, silanetriol or trialkoxysilane-containing radical as stabilizer substance on the surface of the superparamagnetic particles. The stabilizer substance must be made up in such a way that it is miscible with water and keeps the spacing of the magnetic particles sufficiently great for the kinetic energy of the magnetic particles to be greater than the magnetic energy of interaction. The stabilizer substances can be selected from the following substances:

(i) the compounds corresponding to the general formula

X—R—A—B wherein

X represents a functional group selected from the alkoxy, alkylamino and alkylthio group in which the number of carbon atoms in the alkyl part of these groups lies in the range of 1 and 4, or a functional group selected from the hydroxyl, amine, aldehyde, dimethylacetal, diethylacetal, epoxy, thiol, carboxy, 4,6-dichlorotriazine, hydroxamic acid, isocyanate, acylazide, anhydride, diazonium salt, iminocarbonate and toluene sulphonate group;

R is absent or

R is a polyalkylene glycol, a water-miscible polypropylene glycol radical or a water-miscible block copolymer radical of polyethylene glycol (PEG) and polypropylene glycol (PPG), selected from the block copolymers $(PEG)_a\text{-}(PEG)_b, (PEG)_a\text{-}(PPG)_b\text{-}(PEG)_a, (PPG)_b\text{-}(PEG)_a\text{-}(PPG)_b$ wherein a is a positive integer in the range of 1 to 100 and b is a positive integer in the range of 1 to 20;

n is a positive integer, selected for PEG in the range of 4 to 300, for PPG in the range of 3 to 12 and for PEG-PPG block copolymer in the range of 3 to 140; or R is a carbohydrate radical, selected from the monosaccharides glucose, fructose, ribose, desoxyribose, inositol, from the oligosaccharides saccharose, raffinose, gentianose, malecitose, stachyose, verbascose, from the polysaccharides starch, lichenins, glycogen, dextrins, dextrans, inulins, fructosans, lavans, manans, galactans, xylans, arabans, pectins, macropolysaccharides, glycoproteins, from polyuridenylic acid, polyglucuronic acid, polygalacturonic acid, polymannuronic acid and/or alginic acid;

A is absent or

A is an alkyl, alkoxy, acyl, acylamine, alkylamine group, in which the number of carbon atoms in the alkoxy, acyl, acylamine, alkyl group lies in the range of 1 to 4;

B is a phosphorus-containing radical selected from monophosphate, diphosphate, polyphosphate, phosphonate, thiophosphate, thiophosphonate or a carboxylate-, sulphate-, sulphonate-, mercapto-, silanetriol or trialkoxysilane-containing radical; (ii) the phosphate group-containing nucleotides mono-, di-, tri-phosphoric acid esters or mono-, di-, tri-phosphoric acid ester chlorides of adenosine, guanosine, cytidine, uridine, thymidine, desoxyadenosine, desoxyguanosine, desoxycytidine, desoxythymidine, inosine, pyrimidine, cytosine, uracil, thymine, purine, adenine, guanine, methylcytosine, 5-hydroxymethylcytosine, 2-methyladenine, 1-methylguanine, thiamine, flavin, riboflavin and pyridoxalphosphate, pyridoxamine phosphate, ribonucleic acid, ribonucleic acid sequences, desoxyribonucleic acid, desoxyribonucleic acid sequences;

(iii) the silicate group-containing compounds of orthosilic acid and the condensation products thereof; and/or (iv) X—R—A—B is mercaptopurine, -cytosine, -guanine, -uracil, -thymine, -hypoxanthine and the mercapto-nucleosides thereof and the mercapto-desoxynucleosides thereof;

(v) X—R—A—B is a polyaminocarbohydrate.

Examples of stabilizer substances include (vi) mono- and di-[ω-ethylamino-polyethylene glycol]-diphosphate [molecular weight (MW) of the PEG about 1500], mono- and di-[ω-ethyoxy-polyethylene glycol]-thiophosphate (MW of the PEG about 1000) or mono- and di-[ω-methoxy-polyethylene glycolpolypropylene glycol]-phosphate, produced from polyglycol M41/40 (trade name belonging to Hoechst, Germany), mono- and di-[ω-hydroxy-polyethelene glycol]-phosphate (MW PEG about 1500), mono- and di-[ω-oxoethoxy-polyethylene glycol] phosphonate or the acetals thereof (MW PEG about 2000), mono- and di-[ω-oxoethylamino-polyethylene glycol]-phosphate or the acetals thereof (MW PEG about 750), mono- and di-[ω-aminoalkoxy-polyethylene glycol]-thiophosphate (MW PEG about 1000), mono- and di-[ω-hydroxy-polyethylene glycol polypropylene glycol] phosphate, produced from Synperonic F68 (trade name belonging to ICI, Great Britain), mono- and di-[ω-methoxy-polyethylene glycol]-diphosphate (MW PEG about 1000), the dimethylacetal of mono-[ω-oxoethoxy-polyethylene glycol]-diphosphate (MW PEG about 2000), mono-[ω-ethoxy-polyethylene glycol]-polyphosphate (MW PEG about 2000) or mono-[ω-methoxy polyethylene-glycol polypropylene glycol diphosphate, produced from polyglycol M 41/40 (Hoechst, DE).

These reactive polyalkylene glycol-containing stabilizer substances can also be used with their hydroxyl, carbonyl or amino groups for the introduction of other reactive functional groups such as, for example, the thiol, epoxy, carboxy, 4,4,6-dichlorotriazine hydroxamic acid, isocyanate, acylazide, anhydride, diazonium salt, iminocarbonate, toluene sulphonate groups, in order to produce other binding sites on the tissue-specific and pharmacologically active substances;

(ii) from the phosphate group-containing nucleotides mono-, di-, tri-phosphoric acid esters or mono-, di-, tri-phosphoric acid ester chlorides of adenosine, guanosine, cytidine, uridine, thymidine, desoxyadenosine, desoxyguanosine, desoxycytidine, desoxythymidine, inosine, pyrimidine, cytosine, uracil, thymine, purine, adenine, guanine, methylcytosine, 5-hydroxymethylcytosine, 2-methyladenine, 1-methylguanine, thiamine, flavin, riboflavin as well as pyridoxalphosphate, pyridoxamine phosphate, ribonucleic acid, ribonucleic acid sequences, desoxyribonucleic acids, desoxyribonucleic acid sequences;

(iii) from the phosphate, diphosphate, polyphosphate and thiophosphate-, carboxylate-, sulphate-, sulphonate-, mercapto-, silane triol- or trialkoxysilane group-containing carbohydrates, the carbohydrate radicals consisting of the monosaccharides glucose, fructose, ribose, desoxyribose, inositol, of the oligosaccharides saccharose, raffinose, gentianose, malecitose, stachyose, verbascose, of the polysaccharides starch, lichenins, glycogen, dextrins, dextrans, inulins, fructosans, lavans, mannans, galactans, xylans, arabans, pectins, macropolysaccharides, glycoproteins, of polyuridenylic acid, polyglucuronic acid, polygalacturonic acid, polymannuronic acid and/or alginic acid; or from several of these radicals.

According to the invention, tissue-specific binding substances or pharmacologically active substances can be coupled to the stabilizer substances bound to the superparamagnetic particle surface if the stabilizer substances carry at least two chemically reactive functional groups, the phosphate, diphosphate, polyphosphate, thiophosphate, phosphonate, thiophosphonate, carboxylate, sulphate, sulphonate, mercapto, silanetriol or trialkoxysilane group serving for chemical binding to the superparamagnetic particles and the remaining reactive functional groups which consist, for example, of hydroxyl, amine, aldehyde, epoxy, thiol, carboxy, 4,6-dichlorotriazine, hydroxamic acid, isocyanate, acylazide, anhydride, diazonium salt, iminocarbonate, toluene sulphonate groups, serving for the binding of tissue-specific binding substances and pharmacologically active substances.

Such stabilizer substances include, for example, mono-, oligo- or polysaccharide phosphates, carboxylates, sulphates, sulphonates, thiols, silanetriols or trialkoxysilanes, which are provided with the corresponding function groups before or after chemical binding on the superparamagnetic particle surface. The above-mentioned stabilizer substances also include the corresponding polyacids. The introduction of the functional groups into the stabilizer molecules is a known state of the art.

In addition to these reactive stabilizer substances based on carbohydrates, it is possible to use reactive phosphate group-containing biomolecules such as, for example, pyridoxal phosphate, pyridoxamine phosphate or co-carboxylase; mercapto group-containing substances such as mercaptopurine, -cytosine, -guanine, -uracil, -thymine, -hypoxanthine, as well as their mercapto-nucleosides and their mercapto-desoxynucleosides; silanetriol or trialkoxysilane group-containing substances such as ω-ethylamino-polyethylene glycol-trimethoxysilane (MW of the PEG about 1000), ω-methoxy-polyethylene glycol-trimethoxysilane (MW of the PEG about 750) or ω-methoxy-polyethylene glycolpolypropylene glycol-thioethyl-triethoxysilane, produced from polyglycol M41/40 (Hoechst), ω-hydroxy-polyethylene glycol-silanetriol, 3-chloropropyl-trimethoxysilane, 2-mercaptopropyl-triethoxysilane, 3-aminopropyl-triethoxysilane, 3-(2-aminoethylamino) propyl-trimethoxysilane, vinyl-triethoxysilane, vinyl-tri (methoxyethoxy) silane, methacryloxypropyl-trimethoxysilane, or poly-trialkoxysilyl-starch, polytrialkoxysilyl-dextran, poly-trialkoxysilyl-dextrin; sulphate group-containing substances such as dextran sulphate, dextrin sulphate, inulin sulphate; carboxylate group-containing substances such as polycarboxydextran, polycarboxydextrin, polycarboxyamylopectin; polyamino group-containing substances such as polyaminodextran; silicate group-containing compounds of orthosilisic acid and their condensation products, sodium or potasssium silicate solution or alkaline solutions of alkali silicates with condensable hydroxoaluminates being used to stabilize the superparamagnetic particles here; as well as the polycompounds thereof.

According to the invention, tissue-specific binding substances such as, for example, antigens, antibodies, haptens, protein A, protein G, endotoxin-binding proteins, lectins, selectins, can be coupled to the stabilizer molecules which are chemically bound with their monophosphate, diphosphate, polyphosphate, phosphonate, thiophosphate, thiophosphonate, carboxylate, sulphate, sulphonate, mercapto, silanetriol or trialkoxysilane groups to the superparamagnetic particle surface.

Pharmacologically active substances such as, for example, antitumour proteins, enzymes, antitumour enzymes, antibiotics, vegetable alkaloids, alkylation reagents, antimetabolites, hormones and hormone antagonists, interleucines, interferons, growth factors, turmour necrosis factors, endotoxins, lymphotoxins, urocinases, streptocinases, plasminogen-streptocinase-activator-complex, tissue plasminogen-activators, desmodus-plasminogen-activators, macrophage-activator bodies, antisera, protease inhibitors, radioactive phosphorus $^{32}P$-containing stabilizer substances, surfactants or pharmacologically active cells such as, for example, organelles, viruses, microbes, algae, fungi, in particular erythrocytes, thrombocytes, granulocytes, monocytes, lymphocytes, Langerhans islets or pharmacologically active complex forming agents from the group comprising polycarboxylic acids, aminocarboxylic acids, porphyrines, catecholamines or cell fusion facilitating substances can be coupled to the reactive stabilizer substances individually or in addition to one another.

As cell fusion facilitating substances, polyethylene glycols, for example, in concentrations above 25% by weight of the type occurring in even higher concentrations in the stabilizer substance layers of the superparamagnetic particles bring about cell fusion which can lead to further damage to the tumour tissue if the polyethylene glycol-containing superparamagnetic particles are concentrated in tumours.

According to the invention, phosphate or phosphonate group-containing drugs can also be chemically bound to the surface of the superparamagnetic particles, for example estramustin or diethylstilbestrol-diphosphate, in addition to the stabilizer substances.

The toxicity of these pharmacologically active substances can be relatively high as the magnetic particles are preferably concentrated at the corresponding binding sites owing to their tissue-specific interaction or are conveyed to the active site by magnetic drug targeting and concentrated. The dose of the pharmacologically active substances can be kept small as the substance is concentrated at the active site and the remainder of the body is only slightly affected.

The coupling of pharmacologically active substances to the superparamagnetic particles has the further advantage that the progress of treatment can be observed by nuclear spin diagnosis via the reduction in the relaxation time.

The superparamagnetic particles are produced by intentional agglomeration of superparamagnetic single-domain particles. The superparamagnetic single-domain particles are stirred in water and aggregated at a pH of 3 to 7 by heating to between 50 and 120° C. at temperatures above 100° C. in autoclaves. After cooling of the dispersion, the particles are washed until the electrical conductivity of the filtrate is <10 μS/cm. The superparamagnetic particles produced in this way immediately form a rapidly sedimenting precipitate which cannot be converted into a stable dispersion even by vigorous stirring or by ultrasonic treatment. On the chemical binding of phosphate, diphosphate, polyphosphate, thiophosphate, phosphonate, carboxylate, sulphate, sulphonate, thiol, silanetriol or trialkoxysilane group-containing stabilizer substances on the surface of the superparamagnetic particules permits rapid dispersion and, with some stabilizer substances, even with slight stirring with the glass rod.

Depending on the sphere of application, the magnetic dispersions can be dialyzed in order to remove the excess content of stabilizer substance. Dialysis is necessary, in particular, with chemically reactive superparamagnetic particles which are to be used for the coupling of tissue-specific binding substances and pharmacologically active substances.

The stabilized superparamagnetic particle dispersions contain the superparamagnetic single-domain particles which have not yet aggregated or have only slightly aggregated. These single-domain particles form a stable magnetic liquid which can easily be separated from the larger superparamagnetic particles by sedimentation in a magnetic field of appropriate strength and inhomogeneity.

In a simple form of magnetic separation, a beaker with the magnetic dispersion is placed on a permanent magnet having a magnetic flux density of 0.1 mT and the supernatant magnetic liquid is poured off after a sedimentation time of about 30 minutes. The superparamagnetic particles remain behind and are spontaneously redistributed in the dispersion or remain behind as a deposit in the beaker, depending on the particle size. The superparamagnetic particles are redistributed simultaneously or with slight stirring in the aqueous dispersant up to particle sizes of about 500 nm. Superparamagnetic particles larger than about 500 nm can easily be dispersed by more vigorous stirring or ultrasonic treatment.

The sedimentation stability of the superparamagnetic particles according to the invention is significantly higher than with the formerly known magnetic particles having comparable magnetic properties, which is probably due to the strong structuring of the water molecules surrounding the superparamagnetic particles and the thus increased Stokes' particle diameter.

Owing to the small content of stabilizer substance, the magnetic properties of the superparamagnetic particles are stronger than in the magnetic particles known hitherto. As the content of superparamagnetic single-domain particles is significantly higher than in formerly known magnetic particles, the separation rate of the superparamagnetic particles in an inhomogeneous magnetic field is also higher. In a 10% by weight aqueous dispersion of superparamagnetic particles with a diameter of about 100 nm and a magnetite content of 95%, the separation time of the magnetic particles on a permanent magnet having a magnetic flux density of 0.1 mT is less than 1 minute.

The superparamagnetic particles according to the invention have iron oxide contents of 90 to 98% by weight. This denotes a considerable improvement in the magnetic properties relative to the prior art where magnetic particles can contain up to 50% by weight of iron oxide. The new superparamagnetic particles can therefore be correspondingly smaller than the formerly known magnetic particles with the same magnetic interaction. The specific surface area increases and more pharmacologically active substances or tissue-specific binder substances can be coupled on the surface. As the particle size diminishes, the biological compatibility improves and the decomposition rate in the body is increased. The free available time for the magnetic particles during magnetic drug targeting, i.e. the time until the particles are bound by the reticuloendothelial system, also increases as the particle size decreases.

The biocompatibility of the superparamagnetic particles in the body is only a few minutes, i.e. the reticuloendothelial system binds the superparamagnetic particles very rapidly. Macrophages and neutrophilic granulocytes receive magnetizable properties if they adhere to the superparamagnetic particles. This adhesion is conditional on the stabilizer substances of the superparamagnetic particles being bound onto the receptors of the macrophages and the neutrophilic granulocytes. If such binding takes place, the magnetized macrophages and neutrophilic granulocytes can be moved by means of magnetic fields. The macrophages and the neutrophilic granulocytes can penetrate the endothelial barrier in the high endothelium venols and into the tissue. With magnetized macrophages and neutrophilic granulocytes, this process can be assisted by the effect of a magnetic field. During the magnetic drug targeting of tumours with the superparamagnetic particles according to the invention, therefore, accelerated concentration of the magnetized macrophages and neutrophilic granulocytes in the tumour tissue can take place and initiate immunological destruction of the tumour tissue.

Mechanical forces which are proportional to the difference in permeability between the contacting materials and the square of the active magnetic field strength occur at the phase boundary between the superparamagnetic particles and diamagnetic cells.

As the particles according to the invention have a very high content of superparamagnetic particles and the stabilizer substance only has a monomolecular layer of a few nanometers thickness, forces which can lead to destruction of the cells occur at the phase boundaries to diamagnetic cells. These forces can lead to destruction of tumours, for example during the concentration of the superparamagnetic particles in tumours. This magnetomechanical effect could also cause surface molecules of the tumour tissue to be bound and withdrawn by the superparamagnetic particles in the event of a strong interaction between the stabilizer substance of the superparamagnetic particles and the tumour tissue. If these superparamagnetic particles are phagocyted by the macrophages and the neutrophilic granulocytes, the surface molecules of the tumour can be recognised as antigens even if they had not otherwise been identified as antigens by the immune system. A more or less strong immune response by the body to the surface molecules of the tumour and therefore destruction of the tumour can occur.

Stimulation of the immune system by magnetomechanical effects can also be achieved by mixing viruses, bacteria or fungi in vitro with reactive superparamagnetic particles. Thus, superparamagnetic particles which have been stabilized, for example with mono-[ω-oxoethoxy-polyethylene-glycol]-phosphate, can therefore enter covalent chemical bonds with the amino groups of the surface proteins of the viruses or bacteria. Surface molecules of the virus, bacteria or fungus surfaces can be produced with the superparamagnetic particles by the action of strong homogeneous magnetic fields or by means of known cell digestion methods. These superparamagnetic protein fragments are absorbed by the reticuloendothelial system when injected into the body, the protein fragments are recognised as antigens and the body reacts with a corresponding immune response, among other things by the production of appropriate antibodies. Therefore, an immune response in the body can also be stimulated by proteins which have not been recognised as antigens as such by the body. This is particularly important in the production of an immune defence in the body against tumour cells, viruses, bacteria, yeasts or fungi for which there is not yet any suitable chemotherapy and in which resistance against known used drugs has developed.

Immune-stimulating superparamagnetic molecule complexes which can lead to the immune stimulation and destruction of biological active cells during in vivo application can be obtained by coupling reactive superparamagnetic particles to the surface molecules of, for example, tumour cells, viruses, bacteria, yeasts, fungi and by separating these surface molecules using strong inhomogeneous magnetic fields or known cell digestion processes.

Diphosphate or polyphosphate-containing stabilizer substances based on polyalkylene glycols are new compounds and even have a tumour-destroying effect.

Thus, tumours in mice were destroyed during the in vivo application of these stabilizer substances. The tumour-destroying effect can be reinforced by coupling these stabilizer substances to the superparamagnetic particles in that the concentration of the stabilizer substance in the tumour increases significantly owing to magnetic drug targeting. In addition to an increase in the tumour-destroying effect owing to the magnetic drug targeting, a considerable reduction in the active time to incipient visible tumour destruction is also observed.

The stabilizer substances can easily be produced according to the prior art.

The polyethylene glycols are produced by oxethylation of a reactive organic starting compound such as, for example, 2-methoxyethanol, aminoacetaldehyde-dimethylacetal, 2-methoxyethylamine, 2-aminoethanol with ethylene oxide. See Houben-Weyl, volume XIV/2, pages 425 et seq (1963).

The introduction of the phosphate, diphosphate, polyphosphate or thiophosphate group into the polyethylene glycols is easily carried out by reaction with various phosphorylation reagents at room or elevated temperatures. See Houben-Weyl, volume XII/2, pages 131 et seq (1964), volume E2, XII/2, pages 300 et seq (1982).

Phosphate group-containing carbohydrates and phosphate group-containing polysaccharide carboxylic acids are produced in a similar manner (see U.S. Pat. No. 2,970,141).

Alcohols corresponding to dimethylacetals are preferably used as starting materials in the production of ω-oxoalkoxy-polyethylene glycol phosphates, in order to protect the oxo group during ethoxylation and during the introduction of the phosphate or phosphonate group. The acetals can be liberated by acidic hydrolysis with acids or by careful cleavage with ion exchangers. See Houben-Weyl, volume VI/3, pages 203–293 (1964).

The phosphonate group-containing polyethylene glycols can be produced by many methods. See G. M. Kosolapoff, L. Maier, Organic Phosphorous Compounds. Wiley Inters., New York, 1972–1976, volume 7, pages 1–486 (1976), Houben-Weyl, volume XII/1, pages 338–619 (1963), Houben-Weyl, volume E2, pages 300–486 (1982), and in particular DE-A-3407565, DE-A-2424453 and DE-A-3203309.

The silicate group-containing organic substances are produced, for example, by reaction of lithium- or sodium-organic compounds corresponding to the general formula X—R—Li or X—R—Na with tetraalkoxysilanes or tialkoxychlorosilanes (see Houben-Weyl, volume XIII/5, pages 180 et seq (1980)). A further simple method of producing silicate group-containing organic compounds is the reaction of the X—R-(p-toluene sulphonate) with, for example, 2-mercaptopropyl-triethoxysilane, 3-aminopropyl-triethoxysilane in an alkaline medium (see K. Nilsson, K. Mosbach; Eur. J. Biochem. 112, 397–409, 1980).

The mercapto group-containing organic substances are produced, for example, from the X—R-halogen compounds by reaction with thiourea and subsequent alkaline hydrolysis to the corresponding mercapto compounds (see Houben-Weyl, volume IX, pages 3 et seq (1955), volume E2, XI E, pages 32 et seq (1985)).

The polycarboxylic acid group-containing carbohydrates are produced by oxidation of the carbohydrates, for example with potassium permanganate, iron (II)-salts/hydrogen peroxide, periodic acid (see A. H. Haines, Editor, Methods for the Oxidation of Organic Compounds, Academic Press, London, 1988).

The silicate group-containing inorganic condensation products are produced by mere mixing of sodium silicate solution with, for example, sodium aluminate.

The polysulphate group-containing carbohydrates are produced, for example, by chlorosulphonation of carbohydrates.

The main sphere of application of the superparamagnetic particles according to the invention is the sphere of magnetic drug targeting. Owing to the very high content of magnetic material (90 to 98% by weight), even small magnetic particles can be concentrated very well and very rapidly in specific regions of the body by means of electromagnetic or permanent magnetic fields. When pharmacologically active substances are coupled with superparamagnetic particles, their concentration can be drastically increased at the site of action. This fact is particularly important in the treatment of cancer as the substances used for the chemotherapy of tumours have very pronounced side effects on the entire organism and, when concentrated at the site of action, the remainder of the body is less markedly affected by cytostatics.

The superparamagnetic particles can be used for immune activation in the body when coupled with viruses, cells and their surface molecules, the effect of magnetic fields assisting immune activation.

The reactive superparamagnetic particles can also be used for in vitro diagnosis if the corresponding diagnostic substances are chemically bound to the surface of the particles. Owing to the pronounced magnetic interaction with magnetic fields, very small superparamagnetic particles can also easily be separated from the reaction mixture again after a diagnostic reaction.

The superparamagnetic particles can also be used as contrast agents for nuclear spin diagnosis.

During magnet drug targeting the concentration of the superparamagnetic particles to be used is dependent on the particle size, the composition of the stabilizer substances, the magnetic field strength at the active site and the distance between the injection site and the active site. In order to achieve necrosis of a tumour in bare mice, a quantity of injection fluid of about 0.01 to 0.2 percent by volume of the blood volume is necessary, the magnetic saturation induction being about 5 mT.

The quantities of superparamagnetic particles during application as a contrast agent for the MRI are about 0.001 percent by volume of the blood volume when the magnetic saturation induction is about 5 mT.

The production of the superparamagnetic particles according to the invention will be described by examples.

EXAMPLE 1

Iron (III) chloride (270 g) and iron (II) chloride (119 g) are dissolved in 1 l of distilled water. The pH of the solution is adjusted to 9.6 by addition of ammoniacal liquor while stirring. After precipitation has taken place, the dispersion is adjusted to pH 6.0 by hydrochloric acid and the dispersion is heated to 100° C. After cooling, the precipitate is washed with distilled water until the electrical conductivity is <10 μS/cm. The superparamagnetic particles formed consist of $Fe_3O_4$. They can be stabilised.

EXAMPLE 2

Iron (III) chloride (270 g) and iron (II) sulphate (153 g) are dissolved in 1 l of distilled water. The pH of the solution is adjusted to 9.0 by addition of ammoniacal liquor while stirring. After precipitation has taken place, the dispersion is adjusted to pH 5.0 with hydrochloric while stirring, is reacted with 30% hydrogen peroxide solution (22 ml) and is heated for 30 minutes to 80° C. After cooling of the dispersion, the precipitate is washed until the electrical conductivity is <10 μS/cm. The superparamagnetic particles formed consist of γ-Fe2O3 and can be stabilised.

EXAMPLE 3

Iron (III) chloride (270 g) and zinc chloride (82 g) are dissolved in 1 l of distilled water. A pH of 8.5 is adjusted by addition of sodium hydroxide solution while stirring. After precipitation has taken place, the dispersion is adjusted to pH 4 while stirring with hydrochloric acid and is heated to 110° C. in an autoclave. After cooling of the dispersion, the precipitate is washed until the filtrate has electrical conductivity of <10=μS/cm. The zinc ferrite formed can be stabilised.

The superparamagnetic particles are stabilised by mixing an aqueous or low-boiling polar solvent-containing stabilizer solution with the magnetic particles at room temperature. The stabilizer solution can consist of pure stabilizer substances or of mixtures of stabilizer substances, depending on the desired properties. To accelerate dispersion and stabilisation, the dispersion can be stirred or treated with ultrasound. If low-boiling organic solvents are used, they can be removed by vacuum evaporation or dialysis for removal after stabilisation.

The stabilization of the superparamagnetic particles will be described hereinafter with reference to examples.

EXAMPLE 4

All the magnetite precipitate from Example 1 is introduced into a solution of 50 g mono [ω-methoxy-polyethylene glycol]-phosphate (molecular weight about 1000) in 500 ml of distilled water and is stirred for 5 minutes. The dispersion formed is sedimented for 30 minutes on a permanent magnet having a magnetic flux density of 0.1 T and the supernatant material is aspirated from the magnetic fluid. The sediment on the magnetic field contains the superparamagnetic particles. The superparamagnetic particles can be kept clean by washing several times with distilled water and repeated sedimentation in the magnetic field and can be kept in a close particle size distribution. The superparamagnetic particles have an average particle diameter of 120 nm.

These superparamagnetic particles are very suitable for magnetic concentration in tumours. They can destroy the tumour here by magnetomechanical immune stimulation or additionally by hyperthermia, i.e. by irradiation of electromagnetic rays and heating of the tumour. The superparamagnetic particles can also be used as oral or i.v. contrast agents for MRI.

EXAMPLE 5

All the zinc ferrite precipitate from Example 3 is introduced into a solution of 50 g di-[ω-methoxy-polyethylene glycol]phosphate (molecular weight about 1500) in 500 ml of distilled water and is dispersed for 5 minutes with ultrasound having a power of 100 W. The resultant superparamagnetic particles have a diameter of 310 nm. The dispersion is dialyzed against distilled water and is filtered through a 0.45 μm filter. The resultant product can be used as an oral contrast agent for MRI.

EXAMPLE 6

All the γ-Fe2O3 particles from Example 2 are introduced into a solution of 20 g mono [ω-oxoethoxy-polyethylene glycol]phosphate (molecular weight about 1800), 15 g mono- and 15 g di-[ω methoxy polyethylene glycol]-phosphate (molecular weight about 1000) in 500 ml of distilled water and are dispersed for 5 minutes with an ultrasonic disperser (100 W power). The resultant dispersion is dialyzed against distilled water with a 50 kD filter in order to remove excess stabilizer substances. The non-agglomerated or only weakly agglomerated superparamagnetic single-domain particles which form a stable magnetic fluid are separated by magnetic sedimentation as described in Example 4. The superparamagnetic particles have an average particle diameter of 180 nm.

The superparamagnetic particles produced according to Example 6 can be used for many coupling reactions in which the reactivity of the aldehyde group can be employed. For example, for the coupling of amino group-containing pharmacologically active substances such as streptokinase or plasminogen streptokinase activator complex.

EXAMPLE 7

10 ml of the dispersion from Example 6 having a magnetic saturation induction of 5 mT, are mixed with 30 mg of anistreplase and are allowed to stand for 20 minutes at room temperature. The resultant product can be used for magnetic drug targeting for the dissolution of blood clots.

The reactive superparamagnetic particles produced according to Example 6 are also suitable for the production of substances for magnetic drug targeting in tumour treatment, as will be described in Example 8.

EXAMPLE 8

10 ml of the dispersion from Example 6, with a magnetic saturation induction of 5 mT, are mixed with 10 ml of a 10% by weight MITOMYCIN C solution and are shaken for 30 minutes at room temperature. The resultant product is suitable for magnetic drug targeting against leukaemia.

EXAMPLE 9

10 ml of the dispersion in Example 6 having a magnetic saturation induction of 5 mT are mixed with 10 mg of EPIRUBICIN hydrochloride and are shaken for 20 minutes at room temperature. The resultant product is suitable for magnetic drug targeting in tumour treatment.

Phosphate or phosphonate group-containing drugs can also be chemically bound directly on the surface of the superparamagnetic particles according to the invention in that 0.2 to 0.3 times the quantity of the quantity of stabilizer to be added are added in the form of the drug to the unstabilized precipitate and the corresponding remainder of the stabilizer is added after stirring for 5 minutes with continued stirring.

EXAMPLE 10

All the magnetite precipitate from Example 1 is mixed with a solution of 10 g ESTRAMUSTIN in 250 ml of distilled water and is stirred for 5 minutes. 40 g of di-[ω-methoxy polyethylene glycol]-phosphate (molecular weight about 750) are then dissolved in 250 ml of distilled water, are added to the mixture and stirred for 5 minutes. The resultant dispersion is sedimented for 30 minutes on a permanent magnet having a magnetic flux density of 0.1 mT and the supernatant material is aspirated from the magnetic fluid. The sediment on the magnet contains the superparamagnetic particles and is filtered through a 0.45 μm filter. The resultant product can be used for magnetic drug targeting of carcinoma of the prostate.

EXAMPLE 11

All the magnetite precipitate from Example 1 is introduced into a solution of a mixture of 40 g of mono-[ω-methoxy-polyethylene glycol]-phosphate, -diphosphate and -polyphosphate with a mixing ratio of about 8:1:1 and an average molecular weight of about 750 in 500 ml of distilled water and is stirred for 5 minutes. The resultant dispersion is sedimented for 30 minutes on a permanent magnet having a magnetic flux density of 0.1 T and the supernatant material is aspirated from the magnetic fluid. The sediment on the magnetic field contains the superparamagnetic particles. The superparamagnetic particles can be obtained in a pure form and in a close particle size distribution by washing several times with distilled water and repeated sedimentation in the magnetic field. The superparamagnetic particles have an average particle diameter of 120 nm.

These superparamagnetic particles are very suitable for magnetic concentration in tumours. They can destroy the tumour here by magnetomechanical immune stimulation or additionally by hyperthermia, i.e. by irradiation of electromagnetic rays and heating of the tumour. The superparamagnetic particles can also be used as oral or i.v. contrast agents for MRI.

The superparamagnetic particles can be aggregated at specific selected pH values by using stabilizer mixtures. Thus, the precipitation of the superparamagnetic particles in alkaline tumours can lead to magnetomechanical destruction of the tumours in addition to concentration by magnetic drug targeting if, for example, a mixture of cocarboxylase, mono- and di-[ω-methoxy-polyethylene glycol]-phosphate is used as stabilizer.

EXAMPLE 12

All the magnetite precipitate from Example 1 is introduced into a solution of 15 g mono-, 15 g di-[methoxy-polyethylene glycol]phosphate (molecular weight about 2000) and 12 g cocarboxylase in 500 ml of distilled water and is dispersed for 5 minutes with ultrasound. The resultant dispersion is sedimented for 30 minutes on a permanent magnet having a magnetic flux density of 0.1 T and the supernatant material is aspirated from the magnetic fluid. The sediment on the magnetic field contains the superparamagnetic particles. The superparamagnetic particles can be obtained in a pure form and in a close particle size distribution by washing several times with distilled water and repeated sedimentation in the magnetic field. The superparamagnetic particles have an average particle diameter of 120 nm.

These superparamagnetic particles are very suitable for magnetic concentration in tumours. They can destroy the tumour here by magnetomechanical immune stimulation or additionally by hyperthermia, i.e. by irradiation of electromagnetic rays and heating of the tumour. Magnetic fields can increase the effectiveness of immune stimulation.

The new diphosphate and polyphosphate-containing stabilizer substances according to the invention can be used for destroying tumours alone, i.e. also without being coupled to the superparamagnetic aggregates, during systemic application in the body. A mixture of one or more of the above-described stabilizer substances and a pharmacologically acceptable carrier such as, for example, physiological common salt solution is used for this purpose.

EXAMPLE 13

4 g mono-[ω-methoxy-polyethylene glycol]-diphosphate (molecular weight about 1000) are dissolved in 100 ml of physiological common salt solution and are filtered sterile through a 0.2 μm filter. The resultant fluid is suitable for use in tumour destruction.

EXAMPLE 14

All the magnetite precipitate from Example 1 is introduced into a solution of 50 g of a 40% sodium silicate solution in 500 ml of distilled water and is stirred for 5 minutes. The resultant dispersion is sedimented for 30 minutes on a permanent magnet having a magnetic flux density of 0.1 T and the supernatant material is aspirated from the magnetic fluid. The sediment on the magnetic field contains the superparamagnetic particles. The superparamagnetic particles can be obtained in a pure form and in a close particle size distribution by washing several times with distilled water and repeated sedimentation in the magnetic field. The superparamagnetic particles have an average particle diameter of 120 nm.

These superparamagnetic particles are very suitable for magnetic concentration in tumours. They can destroy the tumour here by magnetomechanical immune stimulation or additionally by hyperthermia, i.e. by irradiation of electromagnetic rays and heating of the tumour. The superparamagnetic particles can also be used as oral or i.v. contrast agents for MRI.

EXAMPLE 15

All the $\gamma$-$Fe_2O_3$ precipitate from Example 2 is introduced into a solution of 20 g 3-mercaptopropyl-trimethoxysilane in 500 ml of distilled water and is dispersed for 5 minutes by ultrasound with a power of 100 W.

The resultant superparamagnetic particles have a diameter of 310 nm. The dispersion is dialyzed against distilled water and is filtered through an 0.45 μm filter. The resultant product can be used for the coupling of monoclonal antibodies.

EXAMPLE 16

All the magnetite precipitate from Example 1 is introduced into a solution of 40 g ω-methoxy-polyethylene glycol-trimethoxysilane (molecular weight 1000) in 500 ml of water and is dispersed for 10 minutes with an ultrasonic disperser (100 W power) while heating to 70° C. The separation of the non-agglomerated or only slightly agglomerated superparamagnetic single-domain particles which form a stable magnetic fluid is carried out by magnetic sedimentation as described in Example 4.

Diamagnetic polyalkylene group-containing pharmacologically active substances can also be bound by adsorption on the polyalkylene glycol group-containing superparamagnetic particles, these substances being desorbed from the surface of the superparamagnetic particles again during magnetic drug targeting under the influence of an inhomogeneous magnetic field. If, for example, doxorubucin monopolyethylene glycol phosphate is bound by adsorption on particles according to Example 5, this product can be used for magnetic drug targeting of cytostatics in tumour treatment.

EXAMPLE 17

All the magnetite precipitate from Example 1 is introduced into a solution of 45 g ω-oxoethoxy-polyethylene glycol-silanetriol (molecular weight about 1800) in 500 ml of distilled water and is dispersed for 5 minutes with an ultrasonic disperser (100 W power). The resultant dispersion is dialyzed against water with a 50 kD filter in order to remove excess stabilizer substances.

The separation of the non-agglomerated or only slightly agglomerated superparamagnetic single-domain particles, which form a stable magnetic fluid, is carried out by magnetic sedimentation as described in Example 4. The superparamagnetic particles have an average particle diameter of 180 nm.

The superparamagnetic particles produced according to this example can be used for many coupling reactions in which the reactivity of the aldehyde group can be employed.

Thus, for example, for the coupling of amino group-containing pharmacologically active substances such as streptokinase or plasminogen-streptokinase activator complex.

EXAMPLE 18

10 ml of the dispersion from Example 17 with a magnetic saturation induction of 5 mT are mixed with 30 mg anistreplase and allowed to stand for 20 minutes at room temperature. The resultant product is suitable for magnetic drug targeting for the dissolution of blood clots.

EXAMPLE 19

10 ml of the dispersion from Example 17 with a magnetic saturation induction of 5 mT are mixed with 10 ml of a 10 mg doxorubicin-containing solution and are shaken for 30 minutes at room temperature. The resultant product can be used for magnetic drug targeting in tumour treatment.

These superparamagnetic particles are suitable for magnetic concentration in tumours and the tumour-destroying cytostatic can act on the tumour in a higher concentration. Tumour destruction can additionally be carried out by hyperthermia, i.e. by irradiation of electromagnetic rays and heating of the tumour. Magnetic fields can increase the effectiveness of immune stimulation.

EXAMPLE 20

All the magnetite precipitate from Example 1 is introduced into a solution of 25 g of a mixture of 70% sodium silicate and 30% sodium aluminate in 500 ml of water and is dispersed for 10 minutes with an ultrasonic disperser (100 W power), while heating to 70° C. After neutralization of the dispersion with dilute hydrochloric acid to a pH of 7, the non-agglomerated or only weakly agglomerated superparamagnetic single-domain particles, which form a stable magnetic fluid, are separated by magnetic sedimentation as described in Example 4. These superparamagnetic particles can be used as oral contrast agents for the gastro-intestinal region.

EXAMPLE 21

All the magnetite precipitate from Example 1 is introduced into a solution of 20 g sodium salt of dextran sulphate (molecular weight 40,000) in 500 ml of water and is dispersed for 10 minutes with an ultrasonic disperser (100 W power) while heating to 70° C., and the non-agglomerated or only weakly agglomerated superparamagnetic single-domain particles which form a stable magnetic fluid are separated by magnetic sedimentation as described in Example 4. These superparamagnetic particles can be used as oral contrast agents for the gastro-intestinal region.

The superparamagnetic particles, when coupled with surfactants, can also destroy cell membranes and thus destroy cells in vitro and in vivo. Examples of suitable surfactants include nonylphenol-polyethylene glycol-phosphate, alkyl- or alkylaryl-polyethylene glycol-sulphates (number of ethylene oxide groups between 5 and 40).

To initiate magnetomechanical immune stimulation in the body, magnetizable leucocytes are administered parenterally into the body and are concentrated by means of magnetic fields at the active site. Owing to the magnetomechanical forces, the magnetized leucocytes, and here in particular the neutrophilic granulocytes and macrophages, are concentrated in the high endothethial venols, penetrate the endothelium in an accelerated manner and penetrate the tissue. Concentration of the magnetizable leucocytes, for example in the tumour tissue, can lead to the immunological destruction thereof. In particular when magnetomechanical destruction of the tumour membrane by the superparamagnetic particles occurs and the tumour membrane fragments are phagocyted by the adjacent neutrophilic granulocytes and macrophages. The formation of tumour antibodies can also lead to the destruction of untreated tumours. Magnetic fields can increase the effectiveness of immune stimulation.

To produce a magnetizable leucocyte concentrate, a leucocyte concentrate is mixed with reactive superparamagnetic particles and is reacted at room temperature or at 37° C.

EXAMPLE 22

100 ml of leucocyte concentrate are mixed with 10 ml of the dispersion from Example 6, mixed with a magnetic saturation induction of 5 mT and allowed to stand for 20 minutes at 37° C. The resultant product can be used for magnetic drug targeting for tumour destruction.

Magnetomechanical immune stimulation can also be carried out, for example, with magnetizable viruses, bacteria, fungi, tumour cells or their magnetizable surface molecules. The magnetizable viruses, cells or their surface molecules can be administered to the body parenterally as they are recognised there by the reticuloendothethial system and are bound by the macrophages and the neutrophilic granulocytes and are phagocyted. As a result of phagocytosis, parts of the surface molecules are conveyed back to the surface of the macrophages as a complex with similarly reused glycoproteins from the main histocompatibility complex, where they are checked by the T-lymphocytes of the immune system, are recognised as antigens and the appropriate immune response against the surface molecules is activated. Immune activation of the body against the corresponding viruses and cells therefore takes place. Magnetic fields can increase the effectiveness of immune stimulation.

Immunisation and treatment of difficultly treatable viral, bacterial or fungal infections can therefore be permitted. Magnetizable viruses or cells are produced by simple mixing thereof with reactive superparamagnetic particles, for example according to Example 6. A pharmacologically active preparation for increasing immunity against viruses and cells is obtained by addition of a pharmacologically acceptable carrier to the magnetizable mixture.

Magnetizable surface molecules of viruses, bacteria or tumour cells are produced by simple mixing of these biological particles with the reactive superparamagnetic particles and subsequent blocking of the remaining reactive groups by suitable physiologically compatible substances. Thus, for example, the excess aldehyde groups of the stabilizer substance according to Example 6 are blocked by addition of a 0.5 molar ethanol aminehydrochloride solution (pH 8.5) to the particle dispersion. The magnetized surface molecules are removed from the digestion dispersion by means of a magnetic field after destruction of the magnetized biological particles by known digestion processes such as pressure digestion, mechanical grinding, osmotic shock treatment. The magnetisable surface molecules are purified by washing several times and separation in the magnetic field. A pharmacologically active preparation for increasing immunity against viruses and cells is obtained by addition of a pharmacologically acceptable carrier to the purified magnetisable surface molecules.

As the viruses, bacteria, fungi, tumour cells and their surface molecules are magnetized in vitro, an immune treatment which is specific to the patient can also be carried out. This is conditional on isolation or concentration of the corresponding viruses and cells from the patient's body.

The superparamagnetic particles, when coupled with surfactants, can also destroy cell membranes and thus bring about cell destruction in vitro and in vivo. Suitable surfactants include, for example, nonylphenol-polyethylene glycol-phosphate, alkyl or alkylaryl-polyethylene glycol-sulphate (number of ethylene oxide groups between 5 and 40).

The main sphere of application of the superparamagnetic particles according to the invention is in the sphere of magnetic drug targeting. Owing to the very high content of magnetic material (90 to 98% by weight), even small magnetic particles can be concentrated very well and very rapidly in specific regions of the body by means of electromagnetic or permanent magnetic fields. When pharmacologically active substances are coupled with the superparamagnetic particles, their concentration at the active site can be drastically increased. This fact is particularly important for the treatment of cancer as the substances used for the chemotherapy of tumours have very strong side effects on the entire organism and the remainder of the body is less markedly affected by cytostatics when enriched at the active site.

The superparamagnetic particles can be used for immune activation in the body by coupling with viruses, cells and their surface molecules, the effect of magnetic fields assisting immune activation.

The reactive superparamagnetic particles can also be used for in vitro diagnosis if the corresponding diagnostic substances are chemically bound to the surface of the particles. Owing to the pronounced magnetic interaction with magnetic fields, very small superparamagnetic particles can easily be removed from the reaction mixture again after the diagnostic reaction has taken place.

The superparamagnetic particles can also be used as contrast agents for nuclear spin diagnosis.

The quantities of superparamagnetic particles are about 0.001% by volume of the blood volume when used as contrast agents for MRI, if the magnetic saturation induction is about 5 mT.

I claim:

1. Superparamagnetic particles, of single-domain particles and stabilizer substances, comprising
    superparamagnetic uncoated single-domain particles selected from the group consisting of iron oxide, iron mixed oxide and iron with a particle size in the range between 3 and 20 nanometers are combined to form stable, decomposable coated aggregates with a particle size of the coated aggregates in the range between 10 and 1000 nanometers,
    wherein the coated aggregates have a monomolecular layer on the surface of the aggregates, and said monomolecular layer consisting of stabilizer substances from the group comprising the phosphate, diphosphate, carboxylate, polyphosphate, thiophosphate, phosphonate, thiophosphonate, sulphate, sulphonate, mercapto, silanetriol, trialkoxysilane group-containing polyalkylene glycols, the carbohydrates or the phosphate group-containing nucleotides, the oligomers thereof or the polymers thereof.

2. Superparamagnetic particles according to claim 1, characterized in that the particle size of the superparamagnetic single-domain particles lies in the range of 3 to 20 nm and the particle size of the superparamagnetic aggregates in the range of 10 to 1000 nm.

3. Superparamagnetic particles according to claim 1, characterized in that the superparamagnetic single-domain particles consist of $\gamma$-$Fe_2O_3$, $Fe_3O_4$, of the iron mixed oxides corresponding to the general formula $MO \cdot Fe_2O_3$, wherein M represents the divalent metal ions Fe, Mg, Be, Mn, Zn, Co, Ba, Sr, Cu or mixtures thereof, of mixed oxides corresponding to the general formula $mFe_2O_3 \cdot nMe_2O_3$, wherein Me represents the trivalent metal ions Al, Cr, rare earth metals or mixtures thereof, or of iron.

4. Superparamagnetic particles according to claim 1, characterized in that the stablizer substances are selected from among
    (i) the compounds corresponding to the general formula

wherein

X represents a functional group selected from the alkoxy-, monoalkylamino, dialkylamino, trialkylamino and alkylthio group in which the number of carbon atoms in the alkyl part of these groups lies in the range of 1 and 4, or a functional group selected from the hydroxyl, amine, aldehyde, dimethylacetal, diethylacetal, epoxy, thiol, carboxy, 4,6-dichlorotriazine, hydroxamic acid, isocyanate, acylazide, anhydride, diazonium salt, iminocarbonate and toluene sulphonate group;

R is absent or

R is a polyalkylene glycol, a water-miscible polypropylene glycol radical or a water-miscible block copolymer radical of polyethylene glycol (PEG) and polypropylene glycol (PPG), selected from the block copolymers

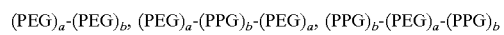

wherein a is a positive integer in the range of 1 to 100 and b is a positive integer in the range of 1 to 20;

n is a positive integer, selected for PEG in the range of 4 to 300, for PPG in the range of 3 to 12 and for PEG-PPG block copolymer in the range of 3 to 140; or R is a carbohydrate radical, selected from the monosaccharides glucose, fructose, ribose, desoxyribose, inositol, from the oligosaccharides saccharose, raffinose, gentianose, malecitose, stachyose, verbascose, from the polysaccharides starch, lichenins, glycogen, dextrins, dextrans, inulins, fructosans, lavans, mannans, galactans, xylans, arabans, pectins, macropolysaccharides, glycoproteins, from polyuridenylic acid, polyglucuronic acid, polygalacturonic acid, polymannuronic acid and/or alginic acid;

A is absent or

A is an alkyl, alkoxy, acyl, acylamine, alkylamine group, in which the number of carbon atoms in the alkoxy, acyl, acylamine, alkyl group lies in the range of 1 to 4;

B is a phosphorus-containing radical selected from monophosphate, diphosphate, polyphosphate, phosphonate, thiophosphate, thiophosphonate or a carboxylate-, sulphate-, sulphonate-, mercapto-, silanetriol or trialkoxysilane-containing radical;

(ii) the phosphate group-containing nucleotides mono-, di-, tri-phosphoric acid esters or mono-, di-, tri-phosphoric acid ester chlorides of adenosine, guanosine, cytidine, uridine, thymidine, desoxyadenosine, desoxyguanosine, desoxycytidine, desoxythymidine, inosine, pyrimidine, cytosine, uracil, thymine, purine, adenine, guanine, methylcytosine, 5-hydroxymethylcytosine, 2-methyladenine, 1-methylguanine, thiamine, flavin, riboflavin and pyridoxalphosphate, pyridoxamine phosphate, ribonucleic acid, ribonucleic acid sequences, desoxyribonucleic acid, desoxyribonucleic acid sequences;

(iii) the silicate group-containing compounds of orthosilic acid and the condensation products thereof; and/or (iv) X—R—A—B is mercaptopurine, -cytosine, -guanine, -uracil, -thymine, -hypoxanthine and the mercapto-nucleosides thereof and the mercapto-desoxynucleosides thereof;

(v) X—R—A—B is a polyaminocarbohydrate.

5. Superparamagnetic particles according to claim 1, characterized in that (i) a tissue-specific binding substances from the group comprising antigens, antibodies, ribonucleic acids, desoxyribonucleic acids, ribonucleic acid sequences, desoxyribonucleic acid sequences, haptens, protein A, protein G, endotoxin-binding proteins, lectins, selectins;

(ii) a pharmacologically active substance from the group comprising antitumour proteins, enzymes, antitumour enzymes, antibiotics, vegetable alkaloids, alkylation reagents, antimetabolites, hormones and hormone antagonists, interleucines, interferons, growth factors, turmour necrosis factors, endotoxins, lymphotoxins, urokinases, streptokinases, plasminogen-streptokinase-activator-complex, tissue plasminogen-activators, desmodus-plasminogen-activators, macrophage-activator bodies, antisera, protease inhibitors and/or radioactive phosphorus $^{32}$P-containing stabilizer substances, surfactants;

(iii) pharmacologically active cells from the group comprising organelles, viruses, microbes, algae, fungi, in particular erythrocytes, thrombocytes, granulocytes, monocytes, lymphocytes and/or Langerhans islets;

(iv) pharmacologically active complex forming agents from the group comprising polycarboxylic acids, aminocarboxylic acids, porphyrins, catecholamines;

(v) phosphate or phosphonate group-containing drugs; and/or (vi) cell fusion facilitating substances are chemically bound onto the superparamagnetic particles.

6. Process for producing superparamagnetic particles of uncoated single-domain particles and stabilizer substances comprising producing superparamagnetic uncoated single-domain particles from iron oxide, iron mixed oxide or iron with a particle size in the range between 3 and 20 nanometers by precipitation from aqueous iron salt solutions with lye or ammoniacal liquor in the pH range of 8.0 to 10.0, adjusting to a pH of between 3 and 6 with an acid and aggregating at a temperature in the range of 50 to 120° C. and optionally elevated pressure in this pH and temperature range, to form aggregates having a particle size in the range between 10 and 1000 nanometers;

purifying the aggregates and reacting with 20 to 50% by weight of stabilizer substances to form coated aggregates, the stabilizer substance being selected from the group comprising phosphate, diphosphate, carboxylate, polyphosphate, thiophosphate, phosphonate, thiophosphonate, sulphate, sulphonate, mercapto, silanetriol, trialkoxysilane group-containing polyalkylene glycols, the carbohydrates or the phosphate group-containing nucleotides, the oligomers thereof or the polymers thereof; and purifying the stable, decomposable coated aggregates obtained in the magnetic field and are optionally further coupled to pharmacologically or diagnostically active substances.

7. Pharmacologically active preparation, of a pharmacologically acceptable carrier and superparamagnetic particles, comprising superparamagnetic uncoated single-domain particles of iron oxide, iron mixed oxide or iron with a particle size in the range between 3 and 20 nanometers, which are combined to form stable, decomposable coated aggregates with a particle size of the coated aggregates in the range between 10 and 1000 nanometers, wherein the coated aggregates have a monomolecular layer on the surface of the aggregates and said monomolecular layer consisting of stabilizer substances from the group comprising the phosphate, diphosphate, carboxylate, polyphosphate, thiophosphate, phosphonate, thiophosphonate, sulphate, sulphonate, mercapto, silanetriol, trialkoxysilane group-containing polyalkylene glycols, the carbohydrates or the phosphate group-containing nucleotides, the oligomers thereof or the polymers thereof, optionally in conjunction with a tissue-specific binding substance, a pharmacologically active substance, a pharmacologically active cell, a pharmacologically active complex forming agent, a drug or a cell fusion-facilitating substance.

8. In a method for destroying tumours and for increasing immunity, optionally under the influence of magnetic fields, the improvement which comprises, administering an effective amount of the pharmacologically active preparation according to claim 7, for said destroying tumors and said increasing immunity.

9. Superparamagnetic particles according to claim 1, wherein the particles are aggregates of $Fe_3O_4$; and wherein the stabilizer substance is methoxy-polyethylene glycol-phosphate Av.MW 1000.

10. Process for producing superparamagnetic particles according to claim 6, comprising utilizing aggregates of $Fe_3O_4$ as said particles; and utilizing methoxy-polyethylene glycol-phosphate Av.MW 1000 as said stabilizer substance.

11. Pharmacologically active preparation according to claim 7, wherein the particles are aggregates of $Fe_3O_4$; and wherein the stabilizer substance is methoxy-polyethylene glycol-phosphate Av.MW 1000.

12. In a method for drug targeting of liver tumors, the improvement which comprises utilizing the pharmacologically active preparation of claim 8, for said drug targeting of liver tumors.

* * * * *

UNITED STATES PATENT AND TRADEMARK OFFICE
CERTIFICATE OF CORRECTION

PATENT NO.   :   5,916,539
DATED        :   June 29, 1999
INVENTOR(S)  :   Herbert Pilgrimm It is certified that error appears in the above-indentified patent and that said Letters Patent is hereby corrected as shown below:

On the Cover Page, Column 1, Line 1 of Item [30],

The date should read --March 2, 1994--, not March 2, 1993".

Signed and Sealed this

Twenty-eighth Day of December, 1999

Attest:

Attesting Officer

Q. TODD DICKINSON

Acting Commissioner of Patents and Trademarks